United States Patent [19]

Tidwell et al.

[11] Patent Number: 4,963,589

[45] Date of Patent: Oct. 16, 1990

[54] METHODS FOR TREATING *GIARDIA LAMBLIA*

[75] Inventors: Richard R. Tidwell; Dieter J. Geratz, both of Chapel Hill, N.C.; Kwasi A. Ohemeng, Clinton, N.J.

[73] Assignee: The University of North Carolina at Chapel Hill, Chapel Hill, N.C.

[21] Appl. No.: 262,324

[22] Filed: Oct. 25, 1988

[51] Int. Cl.$^5$ .................. A61K 31/155; A61K 31/415
[52] U.S. Cl. ..................................... 514/636; 514/397
[58] Field of Search ......................................... 514/636

[56] References Cited

U.S. PATENT DOCUMENTS 4,546,113 10/1985 Glazer ................................. 514/636

OTHER PUBLICATIONS

Chemical Abstracts 86:106191d (1977).
Chemical Abstracts 87:134731u (1977).

*Primary Examiner*—Jerome D. Goldberg
*Attorney, Agent, or Firm*—Leydig, Voit & Mayer

[57] ABSTRACT

This invention relates to a method for treating giardiasis with an aromatic diamidine compound.

5 Claims, No Drawings

METHODS FOR TREATING *GIARDIA LAMBLIA*

BACKGROUND OF THE INVENTION

This invention relates to *Giardia lamblia*, in general, and in particular to a method for treating giardiasis, caused by *Giardia lamblia*.

*Giardia lamblia* is the most frequently identified enteric parasite in the United States. Pediatr. Clin. North AM, Jun. 1988, 35(3), 565–77. It is purportedly the most common pathogenic enteric protozoan and is an important cause of gastro-intestinal disease throughout the world. It is an especially critical problem in third-world countries and presents a particularly difficult problem when it infects children.

In one study of infections in malnourished Jamaican children, in those instances of infection where an aetiological agent was identified, *Giardia lamblia* was the most common enteric pathogen. J. Trop. Med. Hyg., 91(4), 173–80, Aug. 1988. In another study of households located in the Nile Delta region of Egypt, involving 724 children, only one child remained Giardia-negative during the study. Am. J. Epidemiol., 127(6), 1272–81, Jun. 1988.

Unfortunately, although *Giardia lamblia* is such a ubiquitous pathogenic protozoan, inhabiting the upper portion of the small intestines, causing both acute and chronic diarrhea and malabsorption, the presently used therapeutic agents are less than satisfactory. In fact, the therapeutic agents currently of choice were developed principally for treatment of other infections and later found to be efficacious against *Giardia lamblia*. Typically, giardiasis is treated with metronidazole, tinidazole, quinacrine, or furazolidone, but such treatment is typically associated with undesirable side effects and is not always successful.

Pentamidine has been known for decades and was originally shown to be useful for the treatment of trypanosomiasis. Of more recent time, pentamidine has been found to be extremely useful in the treatment of pneumocystis carinii pneumonia, especially in immunocompromised patients suffering from the acquired immunodeficiency syndrome (AIDS). However, pentamidine has not heretofore been known to have utility in the treatment of giardiasis.

It goes without saying that in view of the magnitude of *Giardia lamblia* infection throughout the world, and the lack of a satisfactory agent for the treatment thereof, an urgent need exists for a moreeffective anti-Giardia agent having good therapeutic properties.

SUMMARY OF THE INVENTION

Surprisingly, it now has been discovered that *Giardia lamblia* may be treated with pentamidine and analogues thereof. Accordingly, the present invention provides a method for treating giardiasis which comprising administering to an afflicted host a therapeutically effective amount of compound having the structure of formula I:

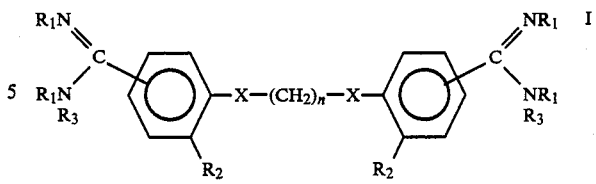

wherein X is O, N or S; $R_1$ is H or two $R_1$ groups on the same amidine group together represent $-(CH_2)_m-$, wherein m=2, 3 or 4; $R_2$ is H, $NH_2$, $OCH_3$, Cl, or $NO_2$; $R_3$ is H, $CH_3$ or $CH_2CH_3$ and n=2−6, or pharmaceutically acceptable salts thereof, or more preferably a compound of formula II:

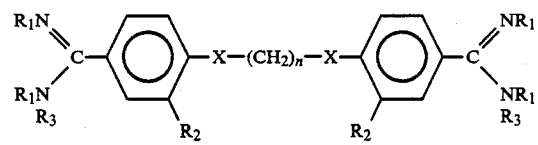

wherein X, $R_1$, $R_2$, $R_3$, m and n have the foregoing meanings, or a pharmaceutically acceptable salt thereof.

DETAILED DESCRIPTION OF THE PREFERRED EMBODIMENTS

The present invention provides a new method for treating giardiasis by administering compounds of formula I, above, or pharmaceutically acceptable salts thereof. Formula I encompasses pentamidine, along with various analogues or derivatives thereof, all of which are aromatic diamidines.

Obviously, the therapeutically effective dosage of any specific compound will vary somewhat from compound to compound and patient to patient. As a general proposition, a dosage from about 0.1 to about 20 mg/kg will have therapeutic efficacy. However, toxicity concerns at the higher level may restrict the dosage to a lower level such as up to about 10 mg/kg, based upon the weight of free-base. Typically, a dosage from about 0.5 mg/kg to about 5 mg/kg will be employed. The duration for the treatment is usually once per day for a sufficient length of time for the patient to become asymptomatic. Depending upon the severity of the infection in the individual patient, this may last anywhere from two to three weeks, or longer.

In accordance with the present method, a compound of Formula I or preferably of Formula II, or a pharmaceutically acceptable salt thereof, may be administered orally as a solid, or may be administered orally, intramuscularly, or intravenously, as a solution, suspension, or emulsion. Alternatively, the compound or salt may also be administered intravenously or intramuscularly as a liposomal suspension. Further, the compound, if hydrophobic, may be administered in an encapsulating hydrophilic liquid which can essentially encapsulate the hydrophobic compound.

Most often, the pharmaceutical compositions useful in the present invention will comprise a compound of Formula I or preferably of Formula II, or a pharmaceutically acceptable salt thereof, in any pharmaceutically acceptable carrier. If a solution is desired, water is the carrier of choice with respect to water-soluble compounds or salts. With respect to water-insoluble compounds or salts, an organic vehicle, such as glycerol, propyleneglycol, polyethyleneglycol, or mixtures thereof, may be suitable. In the latter instance, the organic vehicle may contain a substantial amount of water. The solution in any instance should be sterilized in a suitable manner, preferably by filtration through a 0.22 micron filter. The compositions useful in the practice of the present invention may be provided in the form of vials, ampoules, and the like.

In addition to compounds of Formula I or II, or their salts, the pharmaceutical compositions may contain other additives, such pH adjusting additives, in particular agents such as acids, bases, or buffers, including sodium lactate, sodium acetate, and sodium gluconate. Further, such compositions may contain microbial preservatives, such as methylparaben, propylparaben, and benzyl alcohol. If a multiple use vial is supplied, the pharmaceutical composition should likewise include such a microbial preservative. The formulations may be, of course, lyophilized, using techniques well known in the art.

When the desired pharmaceutical composition employs a compound of Formula I or preferably of Formula II, or a salt thereof, which is water-insoluble, the composition may be supplied in the form of an aqueous based emulsion, containing a sufficient amount of a pharmaceutically acceptable emulsifying agent to emulsify the active compound or salt. Particularly useful emulsifying agents are phosphatidyl cholines and lecithin.

Liposomal formulations may likewise be employed in which the compound of Formula I or preferably of Formula II, or salt thereof, is either water-soluble, and hence entrapped within the hydrophilic center or pore of the liposome, or is water-insoluble and then substantially entrained within the hydrophobic lipid bilayer which forms the structure of the liposomes. Such liposomal formulations may be reduced in size, as through sonication and homogenization, or may be lyophilized, all using techniques well known to those skilled in the art. Alternative, if the compound or salt is hydrophobic, certain hydrophilic liquids which essentially encapsulate the hydrophobic agent at a molecular may be employed.

In terms of the present invention, "water-soluble" is meant to define any composition which is soluble in water in an amount of about 50 mg/ml, or greater and the term "water-insoluble" is meant to define any composition which has solubility in water of less than about 20 mg/ml.

The compounds employed in the present invention in general may be synthesized in manners known and readily understood by those skilled in the art. Therefore, there is no need to explain in great detail the methodology used for the synthesis of most such compounds. Further information regarding appropriate synthesis techniques may be taken from copending application Ser. No. 07/262535, filed Oct. 25, 1988, now U.S. Pat. No. 4,933,347.

It has been found that with respect to the practice of the method of the present invention, treating *Giardia lamblia* with a compound of Formula I or preferably Formula II, or a pharmaceutically acceptable salt thereof, certain compounds appear to possess superior efficacy to others. Pentamidine, for example, has been found to be moderately effective against *Giardia lamblia*, as have most of the compounds within Formula I (or II) above. It was especially surprising to find that the most efficacious product within the scope of the present invention is a compound having a structure as defined by Formula II wherein $X=O$, $R_1$ and $R_3=H$, $R_2=OCH_3$ and $n=3$. Very nearly identical in therapeutic efficacy against *Giardia lamblia* is the compound defined by Formula II wherein $X=N$, $R_1$, $R_2$ and $R_3=H$ and $n=6$. When those compounds are compared to the aforementioned compounds presently of choice for use in treating giardiasis, it is seen that those compounds within the scope of the present invention essentially are as therapeutically efficacious as the current products for treating *Giardia lamblia*.

The present invention will be further described in accordance with the following non-limiting examples.

Examples 1–36 (including comparative examples)

Compounds falling within the scope of Formula I (and II) were obtained, having the structures identified in Tables I through III. To test those compounds against *Giardia lamblia* the following general procedure was employed.

Axenic Culture of Giardia lamblia Trophozoites

*Giardia lamblia* WB strain (ATCC #30957) was grown in filter sterilized TY-S-33 medium (Diamond et al., 1978) modified by the addition of bile (Keister, 1983) and containing 10% heat-inactivated fetal bovine serum and 50 µg/ml ampicillin (Sigma) and 50 µg/ml gentamicin sulfate (Sigma). Stock cultures of trophozoites were grown in $13 \times 100$ mm screw-capped borosilicate glass tubes at 37° C. Organisms were subcultured every 72 hours by chilling the culture tube in an ice-water bath for 5 minutes. The trophozoites were dislodged from the glass by inverting the chilled tube vigorously. The number of organisms per ml was determined by placing 10 µl of the suspension on a hemocytometer. Approximately $5 \times 10^4$ organisms from a logarithmically growing culture were transferred into fresh media.

Chemotherapeutic Agents

Pentamidine and the analogs of pentamidine used in this study were synthesized using the procedures detailed in copending application Ser. No. 07/262,535, filed Oct. 25, 1988, now U.S. Pat. No. 4,933,347. The metronidazole, quinacrine hydrochloride and furazolidone were obtained from Sigma. Stock solutions of 2 mM in modified TYI-S-33 medium were made and further diluted in medium for use in the assays of drug sensitivity.

Microculture of Giardia lamblia

*Giardia lamblia* trophozoites were obtained from logarithmically growing stock cultures. Into the wells of a 96 well U-bottom tissue culture plate (Costar) was placed 100 µl of modified TYI-S-33 medium containing $2.5 \times 10^4$ trophozoites. The tissue culture plate was maintained in an anerobic environment by placing it inside a plastic box modified to allow nitrogen to be passed through the box via inlet and outlet tubing which could be clamped shut. Nitrogen was passed through the box for 2 minutes and the container was placed in a 37° C. incubator gassed with 5% $CO_2$ in air.

$^3$H-thymidine Incorporation Assay of Viability

Varying concentrations of $^3$H-thymidine (0.5, 1.0, 1.5 and 2.0 µCi/well) were added to wells containing $2.5 \times 10^4$ *Giardia lamblia* trophozoites at 2 hour intervals so that it might remain in contact with the trophozoites for 2 to 24 hours. After 24 hours of incubation, the cells were harvested with a multimash cell harvester by washing vigorously with ice-cold Hank's Balanced Salt Solution. Samples were collected on Whatman glass microfiber paper. the paper was air dried, samples were placed in 7 ml scintillation vials and the incorporation of $^3$H-thymidine was determined by liquid scintillation counting. Mean values were calculated from 5 replicates for each time point and concentration. These data were used to determine the optimum time and concentration of $^3$H-thymidine to be used in the assay of drug sensitivity.

Drug Sensitivity Assay

One hundred $\mu$l of modified TYI-S-33 medium containing $2.5 \times 10^4$ trophozoites was placed into each well of a 96-well U-bottom plate. The plates were incubated under anaerobic conditions for 24 hours. After 24 hours, the compounds to be tested were prepared from the 2 mM stock solutions and 100 $\mu$l each solution was added to yield concentrations of 1, 10, 100 and 1000 $\mu$M in the wells. Ten $\mu$l of a 150 $\mu$Ci/ml solution of $^3$H-thymidine (SA=10 Ci/mmole) in modified TYI-S-33 was added 6 hours after the addition of drug to yield a final concentration of 1.5 $\mu$Ci/well. After an additional 18 hours of incubation the cells were harvested. Five replicates were run for each drug concentration and the mean values determined. Non-specific binding of the $^3$H-thymidine to the microfiber paper was determined through the use of control wells to which no organisms were added. The activities of compounds tested were determined by comparing the incorporation of $^3$H-thymidine in the wells to which the compounds were added to that of wells of drug free controls. The drug concentration required to inhibit 50% incorporation of $^3$H-thymidine (IC$_{50}$) was determined (Chou, 1974).

TEST RESULTS

The results of employing the foregoing procedure to determine the efficacy of compounds within the scope of Formula I or II above in treating *Giardra lamblia* are contained in Tables I–III. From those tables it is quite apparent that the very short chain length bridging group wherein n=2 is the least efficacious, at least, when R$_2$=NH$_2$. In Table 1, R$_1$ and R$_3$=H. However, when n=3 very effective results are obtained, whether R$_2$=H, NH$_2$ or OCH$_3$. However, when R$_2$=OCH$_3$, and R$_1$ and R$_3$=H, the most beneficial result is obtained. It is certainly interesting to note then that the second best compound for treating *Giardia lamblia* in accordance with the practice of the present invention C is defined by Formula I wherein X=N, R$_1$, R$_2$ and R$_3$=H, and n=6, showing a relatively long group bridging the two aromatic nuclei.

From Table II it is seen that the meta amidines are comprable to the para-amidines, although somewhat lesser in activity, when the length of the group bridging the aromatic nuclei is in the range of n=4—6. When n=3, the meta amidine is much worse than its counterpart para-amidine. In Table 1, R$_1$ and R$_3$=H.

From Table III it can be seen that the compounds of Formula II wherein the amidine groups have been converted to imidazolines are as a whole slightly less efficacious than their simple amidine counterparts. Thus, comparing Example 5 with Example 31 shows that the imidazoline of Example 31 is slightly less efficacious than the amidine counterpart of Example 5. Also from Table III it is quite apparent that substitution on the imidazoline group, as with a methyl group, leads to drastically reduced efficacy.

Table IV contains efficacy data for three of the compounds currently of choice for treating *Giardia lamblia*. When one compares the efficacy of those compounds with the efficacy data of the most preferred compounds of the present invention, it can be seen that very little if any efficacy difference exists.

TABLE I

GIARDIA LAMBLIA vs. PARA-AMIDINES

| EXAMPLE NO. | X | n | R$_2$ | IC$_{50}$(uM) |
|---|---|---|---|---|
| 1 | O | 2 | NH$_2$ | 1183.8 |
| 2 | N | 2 | NH$_2$ | 743.7 |
| 3 | O | 3 | H | 12.3 |
| 4 | O | 3 | NH$_2$ | 15.4 |
| 5 | O | 3 | OCH$_3$ | 3.2 |
| 6 | N | 3 | H | 68.2 |
| 7 | N | 3 | NO$_2$ | 84.2 |
| 8 | O | 4 | H | 61.6 |
| 9 | O | 4 | NH$_2$ | 96.8 |
| 10 | O | 4 | NO$_2$ | 53.2 |
| 11 | O | 4 | OCH$_3$ | 68.8 |
| 12 | O | 4 | Cl | 27.7 |
| 13 | N | 4 | H | 50.7 |
| 14 | N | 4 | NH$_2$ | 107.7 |
| 15 | O | 5 | H | 76.5 |
| 16 | O | 5 | NH$_2$ | 66.3 |
| 17 | O | 5 | NO$_2$ | 26.1 |
| 18 | O | 5 | OCH$_3$ | 24.0 |
| 19 | O | 5 | Cl | 16.3 |
| 20 | N | 5 | H | 40.6 |
| 21 | N | 5 | NH$_2$ | 48.6 |
| 22 | N | 5 | NO$_2$ | 29.9 |
| 23 | O | 6 | H | 34.3 |
| 24 | O | 6 | NH$_2$ | 38.7 |
| 25 | N | 6 | H | 4.2 |
| 26 | N | 6 | NH$_2$ | 21.9 |

TABLE II

GIARDIA LAMBLIA vs. META-AMIDINES

| EXAMPLE NO. | X | n | R$_2$ | IC$_{50}$(uM) |
|---|---|---|---|---|
| 27 | O | 3 | H | 560.1 |
| 28 | O | 4 | H | 105.8 |
| 29 | O | 5 | H | 55.8 |
| 30 | O | 6 | H | 84.2 |

TABLE III

GIARDIA LAMBLIA vs. PARA-IMIDAZOLINES

| EXAMPLE NO. | X | n | R$_3$ | R$_2$ | IC$_{50}$(uM) |
|---|---|---|---|---|---|
| 31 | O | 3 | H | OCH$_3$ | 25.4 |
| 32 | O | 4 | H | H | 26.0 |
| 33 | O | 4 | CH$_3$ | H | 346.3 |
| 34 | O | 5 | H | H | 39.2 |

TABLE III-continued
GIARDIA LAMBLIA vs. PARA-IMIDAZOLINES

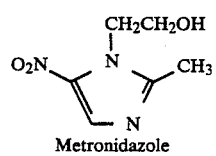

| EXAMPLE NO. | X | n | R3 | R2 | IC50(uM) |
|---|---|---|---|---|---|
| 35 | O | 5 | CH3 | H | 373.3 |
| 36 | O | 5 | H | OCH3 | 47.1 |

TABLE IV
COMPOUNDS CURRENTLY USED TO TREAT GIARDIASIS IN THE US AND THEIR IC50'S DETERMINED BY 3H-THYMIDINE INCORPORATION

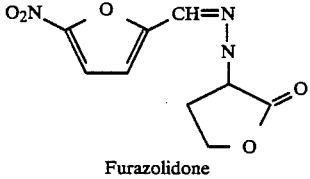

| Metronidazole | Furazolidone | Quinacrine . HCl |
|---|---|---|
| IC50 = 3.65 μM* | IC50 = 1.90 μM* | IC50 = 1.41 μM* |
| IC50 = 0.91 μM | IC50 = 0.74 μM | IC50 = 1.18 μM |
| IC50 = 2.14 μM§ | IC50 = 0.60 μM§ | IC50 = 1.09 μM§ |
| IC50 = 1.08 μM | IC50 = 2.50 μM | IC50 = 1.59 μM |
| IC50 = 2.21 μM± | IC50 = 0.43 μM± | IC50 = 4.02 μM± |

*Stock - WB (ATCC 30957)
Stock - BRIS/83/HEPU/106 (Boreham et al., 1984)
§Stock - BRIS/82/HEPU/41 (Boreham et al., 1984)
Stock - BRIS/83/HEPU/120 (Boreham et al., 1984)
±Stock - BRI/83/HEPU/136 (Boreham et al., 1984)

What is claimed is:

1. A method for treating giardiasis comprising administering to an afflicted host patient a therapeutically effective amount for treating giardiasis of compound having the structure of formula I:

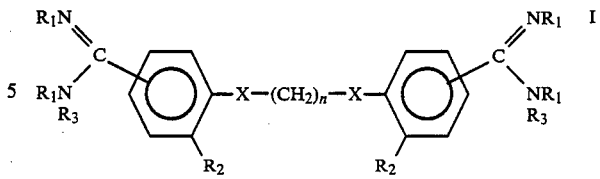

wherein X is O, N or S; $R_1$ is H; $R_2$ is H, $NH_2$, $OCH_3$, Cl, or $NO_2$; $R_3$ is H, $CH_3$ or $CH_2CH_3$ and n=2—6, or a pharmaceutically acceptable salt thereof.

2. The method of claim 1 wherein the compound has the formula

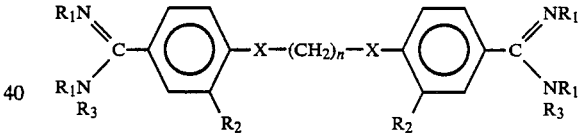

wherein X, $R_1$, $R_2$, $R_3$ and m and n have the foregoing meanings, or a pharmaceutically acceptable salt thereof.

3. The method of claim 2 wherein X=O, $R_1$ and $R_3$=H, $R_2$=$OCH_3$ and n=3.

4. The method of claim 2 wherein X=N, $R_1$, $R_2$ and $R_3$=H and n=6.

5. The method of claim 2 wherein the compound is administered at a dosage level from about 0.1 to about 20 mg/kg, based upon the weight of free-base.

* * * * *

UNITED STATES PATENT AND TRADEMARK OFFICE
CERTIFICATE OF CORRECTION

PATENT NO. : 4,963,589

DATED : October 16, 1990

INVENTOR(S) : Richard R. Tidwell, Dieter J. Geratz and Kwasi A. Ohemeng

It is certified that error appears in the above-identified patent and that said Letters Patent is hereby corrected as shown below:

Please insert in Column 1, after the title, and before "FIELD OF THE INVENTION":

"This invention was made with government support under N01-AI-72648 awarded by the National Institutes of Health. The government has certain rights in the invention."

Signed and Sealed this

Twenty-seventh Day of April, 1993

Attest:

MICHAEL K. KIRK

*Attesting Officer*  *Acting Commissioner of Patents and Trademarks*